United States Patent [19]

Nummy et al.

[11] Patent Number: 5,847,169

[45] Date of Patent: Dec. 8, 1998

[54] PROCESS FOR PREPARING OXIRANEMETHANAMINE DERIVATIVES

[75] Inventors: Laurence J. Nummy; Denis P. Byrne, both of Newburgh, N.Y.

[73] Assignee: Boehringer Ingelheim Pharmaceuticals, Inc., Ridgefield, Conn.

[21] Appl. No.: 843,079

[22] Filed: Apr. 25, 1997

Related U.S. Application Data

[60] Provisional application No. 60/016,867 May 7, 1996.

[51] Int. Cl.⁶ ...................... C07D 303/36; C07D 405/12
[52] U.S. Cl. .......................... 549/521; 546/169; 544/147; 548/311.1; 549/28; 549/60; 549/473
[58] Field of Search ............................. 546/169; 549/521

[56] References Cited

U.S. PATENT DOCUMENTS 5,648,511  7/1997  Ng et al. .................................. 558/345

OTHER PUBLICATIONS

Girijavallabhan et al., Bioorganic and Medicinal Chem., vol. 2(10), pp. 1075–1083 1994.

*Primary Examiner*—Bernard Dentz
*Attorney, Agent, or Firm*—Robert P. Raymond; Alan R. Stempel; Mary-Ellen Devlin

[57] ABSTRACT

A process for preparing oxiranemethane derivatives which are useful as intermediates for preparing aspartyl protease inhibitors comprising the steps of activating an aminodiol, acylating the aminodiol and reacting the acylated aminodiol with a base to form an epoxy compound.

18 Claims, No Drawings

PROCESS FOR PREPARING OXIRANEMETHANAMINE DERIVATIVES

RELATED APPLICATIONS

The benefit of provisional application Ser. No. 60/016,867 filed 7 May 1996 is hereby claimed.

FIELD OF THE INVENTION

The present invention provides a novel process for preparing oxiranemethanamine derivatives which are useful as intermediates for preparing aspartyl protease inhibitors.

DESCRIPTION OF THE RELATED ART

Aspartyl proteases are enzymes which make use of aspartic acid residues in their active site to catalytically hydrolyze specific amide bonds in peptides. The design of molecules which effectively inhibit the function of aspartyl protease enzymes has been carried out in the recent past. These molecules have a strong affinity for the enzyme catalytic site but unlike the natural enzyme substrates they contain an appropriately positioned fragment, "the transition state isostere" (TSI) which is incapable of hydrolytic cleavage. This confers upon these molecules the ability to inhibit the catalytic activity of the enzymes.

HIV protease is a particular aspartyl protease enzyme which has a critical role in maturation and replication of the Human Immunodefficiency Virus. When applied to this enzyme, the inhibitory strategy heretofore described results in clinically significant anti-viral effects.

Many methods of preparing protease inhibitors have been published. One approach is based on the preparation of a reactive precursor to the TSI fragment which can be coupled to other fragments of the intended inhibitor. Examples of the preparation and use of such reactive precursors pertinent to this invention can be found in: J. Org. Chem. 1985, 50, 4615; J. Org. Chem. 1987, 52(8), 1487; EP 346847 (example 19); EP 432964 (examples 1 and 2); J. Med. Chem. 1992, 35, 1685; WO 9323388; J. Med. Chem. 1993, 36, 2300; J. Chem. Soc. Chem. Commun. 1993, 9, 737; J. Org. Chem. 1994, 59, 3656; J. Med. Chem. 1991, 34, 1222; J. Med. Chem. 1992, 35, 2103; J. Org. Chem. 1995, 60(21), 6696.

All of these prior art procedures for the preparation of a reactive precursor to the TSI fragment of HIV protease inhibitors suffer from one or more of the following disadvantages: the use of expensive or inaccessible raw materials, commercially impractical or hazardous reaction conditions and reagents, time consuming multi-step reaction sequences employing unstable and/or dangerous intermediates, production of isomeric mixtures resulting in low yields of pure substance due to lengthy separation procedures that are impractical for larger scale production.

SUMMARY OF THE INVENTION

The inventor has discovered a process for producing a reactive TSI precursor with the formula A:

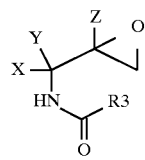

wherein X is hydrogen, an alkyl, cycloalkyl, cycloalkylalkyl, aryl, arylalkyl or arylheteroatomalkyl group where heteroatom is nitrogen, oxygen or sulfur.

Within the context of substituent X and the present application, the term alkyl means a straight or branched chain hydrocarbon containing from 1 to 8 carbon atoms. The term cycloalkyl means a cyclic hydrocarbon containing from 3 to 8 carbon atoms. The term aryl means phenyl, naphthyl, or a 5–6 membered heterocyclic ring containing one or more, and preferably one or two heteroatoms selected from N, O and S. The aryl group can be optionally substituted with one or more alkyl groups, haloalkyl groups, halogens, amino or hydroxy groups. In accordance with the foregoing definition, the group X is exemplified by but not limited to:

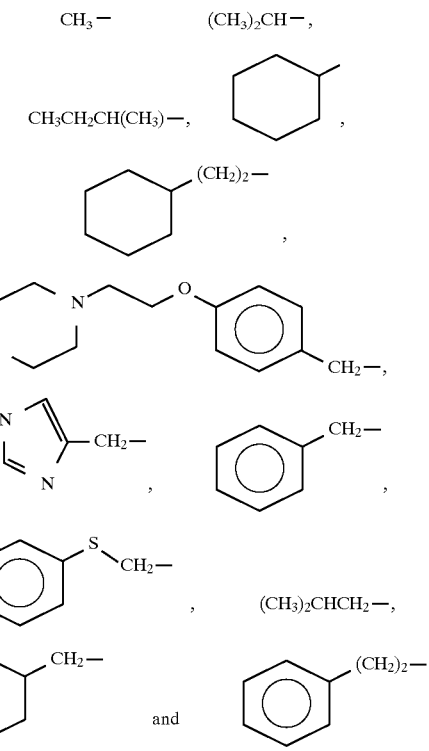

Y and Z are both hydrogen and can independently have a stereochemical orientation which results in either the (R) or (S) configuration (according to the Cahn-Ingold-Prelog nomenclature Cf. Angewandte Chemie Int=l Ed. Engl. 5, 385, (1986)) at the carbon atoms to which they are bound. $R_3$ is lower alkoxy group containing 1 to 8 carbon atoms which can form a straight or branched chain, part of a ring or a combination thereof;

an alkenylmethoxy group;

an arylalkoxy group wherein the aryl portion is optionally substituted with halogen atoms, lower alkoxy or lower alkyl groups of from one to five carbon atoms or combinations thereof;

an aralkyl group where the alkyl portion has from 1 to 5 carbon atoms;

an aryloxyalkyl group wherein the aryl portion is optionally substituted with halogen atoms, lower alkoxy or lower alkyl groups of from one to five carbon atoms or combinations thereof. The alkyl portion contains from 1 to 5 carbon atoms;

an aryl group optionally substituted with heteroatoms or heteroatom groups, alkyl groups, haloalkyl groups, halogen atoms, amino, or hydroxy groups;

an acylated alpha-aminoalkyl group wherein the alkyl group is defined by those found in the naturally occurring aminoacids and the acyl group is derived from a carboxylic acid or carbonic acid ester.

In accordance with the foregoing definition of $R_3$, the group $R_3C(O)$ is exemplified by but not limited to:

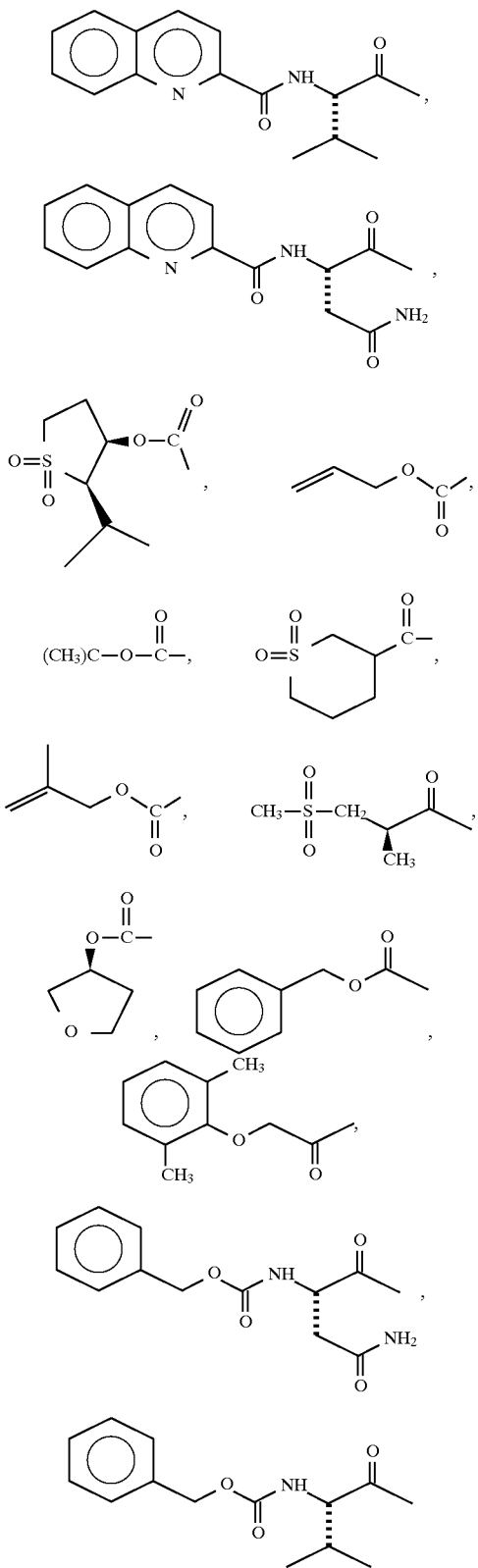

-continued
and

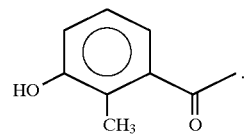

In the context of $R_3$, the term aryl is used to include groups such as substituted or unsubstituted: phenyl, naphthyl, heterocyclic rings containing one or more nitrogen, oxygen or sulfur atoms such as pyridyl, pyrimidinyl, furyl, thienyl, pyrrolyl, thiazolyl, oxazolyl, imidazolyl, quinolinyl, indolyl, benzothiazolyl, benzofuryl, benzoxazolyl, benzimidazolyl and the like.

The term heteroatom groups is defined as a group of covalently bound atoms containing one or more nitrogen, oxygen, sulfur or halogen atoms commonly recognized by those skilled in the art as stable arrangements. Examples of such groups are ethers, sulfides, sulfones, esters, amides, nitriles and the like.

The term halogen includes fluoro, chloro and bromo. The naturally occuring amino acids include lysine, cysteine, leucine, isoleucine, tryptophan, phenylalanine, alanine, histidine, proline, glycine, methionine, serine, tyrosine, threonine, asparagine, aspartic acid, glutamic acid and valine.

These examples serve to illustrate the definition but not to limit the invention in any way.

Accordingly, it is a primary object of the invention to provide an novel process for the production of compounds of formula A.

It is also an object of the invention to provide an improved stereo specific process for the production of compounds of formula A.

It is also an object of the invention to provide an improved process for the production of compounds of formula A which avoids hazardous reaction conditions and sensitive intermediates.

It is also an object of this invention to provide a novel process for the practical large scale production of a compound of formula A.

It is also an object of the this invention to provide a process for the production of compounds of formula A by the direct acylation of intermediates to form an amide without the need to use protection and deprotection steps.

These and other objects of the invention will become apparent from a review of the appended specification.

DESCRIPTION OF THE PREFERRED EMBODIMENTS

The invention provides a convenient method for the production of TSI fragment precursors of formula A or their functional equivalents.

This method makes use of a compound of formula 1:

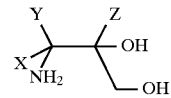

wherein X, Y and Z are as previously defined.

The compound of formula 1 is not obviously convenient as an intermediate for the preparation of compounds with formula A or their equivalents. Those with ordinary skill who would contemplate this conversion recognize that conventional methods require acylation of the amine, selective activation of one hydroxyl group and treatment with a base to form an epoxide. Note that the term "activation" in this context and as used hereafter means to transform the hydroxyl group in such a way that a net displacement of the original oxygen atom from the rest of the molecule becomes possible. This activation is sometimes complicated by poor selectivity in distinguishing the two hydroxyl groups. When this occurs it results in lower yield and higher by-product contamination. The above strategy is typically executed in separate steps with work-up and isolation of intermediates using several reaction vessels. It would be advantageous to avoid this.

The above operations would apply to the preparation of either amide or urethane derivatives. The acylation must precede the activation of the hydroxyl group (ie. by sulfonylation) due to the greater reactivity of the amine. This is problematic if an amide derivative is used in the hydroxyl activation step due to low yields of impure product. To circumvent this, it is necessary to perform the activation on a urethane derivative. This obligates two additional steps in the overall preparation of an amide derivative.

This invention comprises a novel means for activation of the compound of formula 1 followed by an acylation step thereby rendering formula 1 an unexpectedly efficient precursor to known HIV protease inhibitors. The activation strategy employed in this invention obviates the need for more conventional transformations and their associated drawbacks mentioned above. It is advantageous because the activation step is highly selective for the terminal hydroxyl group. The method allows all three steps, activation, acylation and epoxide formation to be performed if desired in a single reaction vessel. This can be conducted using a continuous sequence of operations without work-up and isolation of intermediates. Furthermore, by performing the diol activation prior to amine acylation, protection and deprotection steps can be eliminated when preparing amide derivatives.

A preferred process by which the compound of formula 1 is converted to the compounds of formula A is based on the dehydrative bromination of the compound of formula 1 with substantially anhydrous hydrogen bromide in a carboxylic acid solution at a temperature in the range of 5° to 60° C. for a reaction time in the range of one hour to four days. The hydrogen bromide being present in a mole ratio with respect to a compound of formula 1 ranging from 2 to 10. Examples of carboxylic acids useful for this purpose are formic acid, acetic acid and propionic acid. Most preferable is acetic acid. This activation step produces a product which is a mixture of the bromohydrin compound of formula 2 and the bromoester of formula 3:

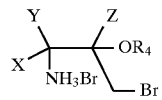

herein $R_4$=H (formula 2); $R_4$=COH, $COCH_3$ or $COCH_2CH_3$ (formula 3.

The product may be used directly without isolation of the hydrobromide salts. The excess acetic acid and hydrogen bromide are distilled from the mixture of the compounds of formula 2 and formula 3 and exchanged with a suitable solvent for reaction with an acylating agent and a base. Solvents can be, but are not limited to methanol, toluene, dichloromethane, tetrahydrofuran, dimethylformamide, acetonitrile or water depending upon the acylating agent and base used. Suitable acylating agents are acyl halides, dicarbonic acid esters, activated esters and intermediates generated in situ from N-protected aminoacids such as mixed anhydrides, acyl isoureas and the like. It is apparent to those skilled in the art of chemical synthesis which type of acylating agent is appropriate, based on considerations of the acyl group to be transferred and the characteristics of the contemplated reagent such as stability and availability. Furthermore, the most effective combination of solvent, acylating agent, base and reaction parameters such as time and temperature depends on the nature of the acyl group to be transferred and the nature of the compound of Formula I. These considerations will be apparent to those familiar with the art.

The acylation reaction mixture produced contains a mixture of acylated bromides which are collectively referred to herein as the Aactivated precursors@ to Formula A. This mixture, without work-up or isolation can be contacted directly with a base to form the epoxide of formula A. Alternatively if desired, the acylation reaction mixture can be subjected to work-up and isolation of the acylated bromides which are contacted with a base in a separate step. In either case, the overall transformation of a compound of formula 1 to a compound of formula A occurs with complete stereochemical fidelity.

Examples of formula A compounds include compounds such as [S-(R*,R*)]-(1-oxiranyl-2-phenylethyl) carbamic acid 1,1-dimethylethyl ester, [S-(R*,R*)]-(1-oxiranyl-2-phenylethyl) carbamic acid phenylmethyl ester, [R-(R*,S*)]-(1-oxiranyl-2-phenylethyl) carbamic acid 1,1-dimethylethyl ester, [R-(R*,S*)]-(1-oxiranyl-2-phenylethyl) carbamic acid phenylmethyl ester, N-[S-(R*,R*)-(1-oxiranyl-2-phenylethyl)]-2-(2,6-dimethylphenoxy) acetamide, N-(quinolin-2-ylcarbonyl-L-valine S-(R*,R*)-(1-oxiranyl-2-phenylethyl)amide, $N^2$-(quinolin-2-ylcarbonyl)-L-asparagine S-(R*,R*)-(1-oxiranyl-2-phenylethyl)amide, [S-(R*,S*)]-(1-oxiranyl-2-phenylthioethyl) carbamic acid 1,1 dimethylethyl ester, [3S-[3R*(1R*,2R*)]]-(1-oxiranyl-2-phenylethyl) carbamic acid tetrahydro-3-furanyl ester, [2R-[2R*,3R*(1S*,2S*)]]-(1-oxiranyl-2-phenylethyl) carbamic acid tetrahydro-[2-[(1-methyl)ethyl]-3-thienyl ester, S,S-dioxide.

These compounds are represented graphically in the same order as the above names as follows:

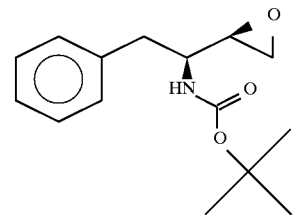

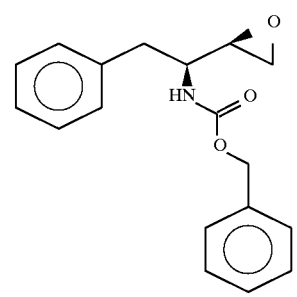

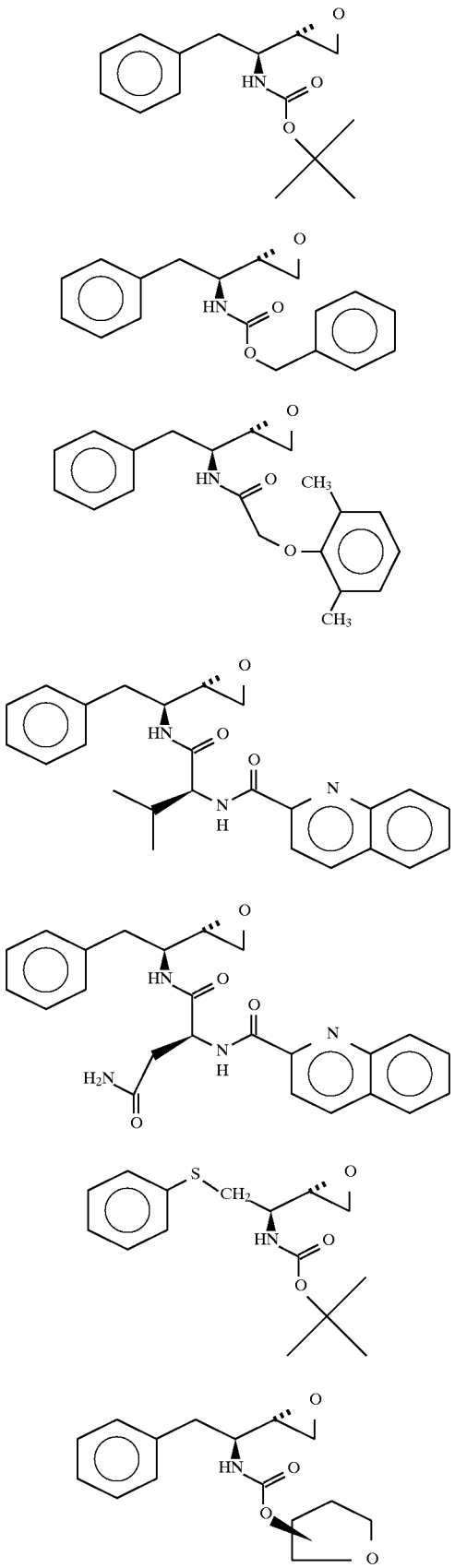

In any instances of ambiguity between the foregoing chemical names for representative compounds of formula A and the graphic representation, the graphic representation should take precedence in establishing the identity.

The compounds of Formula A are converted to aspartyl protease inhibitors in one or more steps depending upon the inhibitor. A pivotal step required in this process involves contacting the epoxide with a nucleophillic agent which induces ring opening and formation of a bond with the terminal carbon of the epoxide. The atom contributed to this new bond from the nucleophilic agent can be a carbon, nitrogen or sulfur atom. Suitable nucleophilic agents are ammonia or primary or secondary amines, mercaptide salts, carbanions generated from carbonyl compounds and the like.

Primary amines may be of the formula $R_5NH_2$ wherein $R_5$ is selected from the group consisting of alkyl, cycloalkyl and arylalkyl. The secondary amines may be of the formula $R_6NHR_7$ where $R_6$ and $R_7$ are independently selected from the group consisting of alkyl, cycloalkyl, arylalkyl and cycloaliphatic amines which may be fused with an aromatic ring where the nitrogen of the cycloaliphatic amine is separated by at least one carbon atom from the aromatic ring.

Such agents are exemplified by but are not limited to benzylamine, iso-butyl amine, cyclopentylmethylamine, piperidine, dimethyl amine, 3S,4aS,8aS-N-(1,1-dimethylethyl)decahydro-3-isoquinolinecarboxamide, 2(S)-{[(1,1-dimethylethyl)amino]carbonyl}-4(R)-[4-(pyridinylmethyl)oxy]piperidine, sodiumdiethylmalonate. Many other nucleophilic agents suitable for this purpose are apparent to one of ordinary skill in the art.

The invention also includes the direct conversion of the mixture of acylated bromides (the epoxide activated precursors) to an aspartyl protease inhibitor or a more advanced intermediate leading to it.

This is brought about by simultaneous or sequential contact with a base and a nucleophilic agent. The epoxide of Formula A is generated in situ. The nucleophilic agents hereinbefore mentioned function in the same manner. Suitable bases for the epoxide formation are alkali metal hydroxides, carbonate, alkoxides and hydrides.

The solvent used for this reaction can be but is not limited to tetrahydrofuran, methanol, ethanol or isopropanol, either substantially anhydrous or mixed with water. The reaction temperature is in the range of minus 10°/C. to plus 90°/ from one to 120 hours.

The compound of formula A is useful as a precursor to protease inhibitors which are described in U.S. Pat. No. 5,196,438, EP 539192-A1, EP 560268, EP 560269, WO 9410134, WO 9418192, WO 9414793, WO 9323379, EP 434365, WO 9405639, WO 9509843, WO 9304043 and U.S. application Ser. No. 08/025,703 filed Mar. 3, 1993 as being useful for the treatment of HIV infections.

The compound of formula 1 may alternatively be reacted with a urethane forming material such as an alkylchloroformate or dialkyldicarbonate to form a urethane which is further acylated with para-toluenesulfonylchloride to form a primary sulfonate ester. This acylation is performed in an organic solvent containing a base. Many choices of solvent and base are possible and familiar to those skilled in the art. The preferred range for the acylation is −25°/C. to +25°/C., most preferably from about −5°/C. to −10°/C. The reaction time is in the range of 1 to 48 hours, most preferably about 24 hours and atmospheric pressure is preferred. The preferred stoichiometry of paratoluenesulfonylchloride based on the diol to be acylated is 100 to 106 mole % and most preferably about 103 mole %. The sulfonate ester may be converted to the epoxy derivative by contacting it with a base in an organic solvent. Suitable bases for the epoxide formation are alkali metal hydroxides, carbonates, alkoxides and hydrides. These compounds are useful for preparation of amide-containing inhibitors such as those which are disclosed in U.S. Pat. No. 5,196,438, EP 560268, EP 560269, WO 9410134, WO 9414793, WO 9323379, EP 434365, WO 9509843, WO 9304043, U.S. application Ser. No. 08/025,703 filed Mar. 3, 1993 by deprotection and acylation, or urethane-containing inhibitors such as those which are disclosed in EP 539192-A1, WO 9418192, WO 9405639 and WO 9308184.

This invention also comprises preparing an aminodiol compound of formula 4

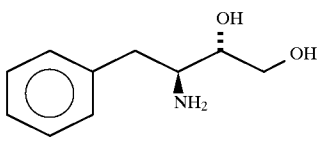

or its enantiomeric form by step (a) which comprises reacting a glycidol compound of the formula:

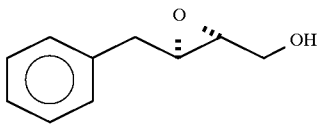

or its enantiomeric form respectively with an amine of the formula: $R_1R_2NH$ wherein $R_1$ and $R_2$ are independently selected from the group consisting of hydrogen, arylalkyl or di-(aryl)alkyl where the aryl portion is attached to the same carbon bearing the amino function and is optionally substituted with lower alkoxy or lower alkyl groups of from 1 to 5 carbon atoms. The alkyl portion is from 1 to 5 carbon atoms optionally substituted with hydroxy or lower alkoxy groups. The reaction is conducted in the presence of a catalyst. In specifying $R_1$ and $R_2$ the term aryl means a phenyl or naphthyl group.

Suitable amines include benzylamine; alpha-methylbenzylamine; dibenzylamine; benzhydrylamine; 1-phenyl-2-hydroxy ethylamine; and the like.

The catalyst may be a transition metal catalyst, which is preferably a titanium (IV) compound such as titanium (isopropoxide)$_4$ at a temperature of 25° to 100° C. Generally, the transition metal catalyst is used at a level which is in excess of one mole equivalent with respect to the amine. The reaction is carried out in the presence of an aprotic organic solvent such as benzene, toluene or xylene.

The reaction of compound 5 with the amine yields a mixture of compounds having the following structures:

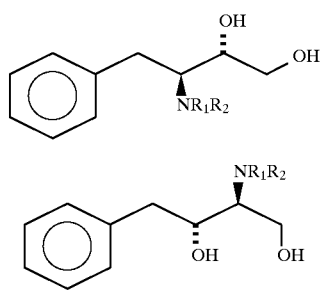

In step (b) the products of step (a) are hydrogenated to replace $R_1$ and/or $R_2$ with hydrogen atoms. The hydrogenation of the compounds of formula 6 and 7 may be carried out using conventional hydrogenation conditions such as hydrogen in the pressure range of 15–100 psi in the presence of a palladium-carbon catalyst at 20° to 35° C. for a period of from 3 to 24 hours.

Thereafter, a compound of formula 4 is crystallized from the reaction mixture, substantially free of its enantiomer and the hydrogenated derivative of the compound of formula 7.

It is surprising and unexpected that the crystallization of the compound of formula 4, substantially free of the hydrogenated derivative of the isomeric compound of formula 7, occurs spontaneously and with high efficiency. No additional purification is required prior to use of the compound of formula 4 as an intermediate and the product may also be stored in solid form for long periods of time without degradation.

The compounds of Formula A and their pharmaceutically acceptable salts may be converted by reaction with a nucleophilic agent as described hereinabove to aspartyl protease inhibitors which may be used as HIV protease inhibitors at a oral dose of 1 mg to about 5.0 g., preferably, 3 mg to 3.0 g and more preferably about 10 mg to about 1.0 g per person daily, given in one to three divided doses (or for example 300 mg per person given once a day or three times a day). The dose may be adjusted depending on the particular compound and the response of the individual patient. The compounds may be prepared in the form of pharmaceutical compositions according to the methods of U.S. Pat. No. 5,196,438, which is incorporated by reference.

The following examples illustrate the invention and are not to be construed as limiting the invention.

EXAMPLE 1

This example demonstrates the continuous three step sequence to prepare a urethane-protected α-phenylmethyloxiranemethanamine.

Preparation of [S-(R*,R*)]-(1-oxiranyl-2-phenylethyl)carbamic acid 1,1-dimethylethyl ester A 1000 mL 3-neck round bottom flask is equipped with a mechanical overhead stirrer, a suck-back trap on both the gas inlet and outlet side of the reactor, a 500 mL gas washing bottle charged with sodium hydroxide solution for scrubbing, and a PVDF-coated type-K thermocouple probe. The reaction vessel is charged with S-(R*,R*)-3-amino-4-phenyl-1,2-butanediol, 50.02 grams (275.9 mmol) followed by glacial acetic acid, 210 mL. The mixture is stirred and the temperature rises from 22° C. to 32° C. At this point, an ice/water cooling bath is placed beneath the vessel to moderate the exotherm. The temperature decreases and most of the solid dissolves. Addition of hydrogen bromide gas, 100.08 grams (1236.9 mmol) via 3" o.d. teflon tube is initiated when the internal temperature is 20° C. The addition requires 50 minutes. During this period, the temperature is maintained between 15° C. and 20° C. The gas cylinder is weighed intermittently to insure the proper charge. The reaction vessel is vented to the scrubber which contains 320.65 g of 6.25% (w/w) sodium hydroxide solution. When gas addition is complete, a check of the gross weight of the scrubber reveals an increase of 0.12 grams (note 1). The resulting pale yellow solution (contains a small amount of undissolved solids) is allowed to stir at ambient temperature. Three hours from the end of hydrogen bromide addition, an aliquot of the reaction solution is withdrawn for analysis (note 2). This reveals the aminodiol is completely consumed.

Twenty-one hours from the end of hydrogen bromide addition, the scrubber is exchanged for one containing 399.8 g of 15% w/w sodium hydroxide solution. The reaction mixture is sparged with nitrogen using a Robu micro-filter candle (40–100 micron porosity) as the temperature is increased from 21° C. to 50° C. The total time for this operation is 2 hours, 45 minutes. During this period, the scrubber increases in weight by 19.33 g. Sparging is discontinued and heating is discontinued.

The reaction vessel is configured for distillation. During the 1 hour, 25 minute interval since sparging is discontinued, the internal temperature drops to 31° C. The pressure is lowered to 40 mm Hg and the vessel is heated to a maximum pot temperature of 60° C. over 1 hour, 40 minutes while volatiles are distilled out. The collected distillate weighs 178.44 g.

The pressure is increased to 80 mm Hg and toluene is charged to the reaction vessel, 175.92 g. Distillation is resumed, maintaining a pot temperature of 45°–50° C. This procedure is repeated with four more charges of toluene, 180.57 g, 177.34 g, 169.35 g and 170.89 g, respectively. The total time for toluene distillation is 2 hours, 10 minutes. When distillation ceases, the residue, a viscous syrup (stirring is not a problem) is cooled to ambient temperature. Stirring is continued for 1 hour, 30 minutes while the last toluene distillate fraction is checked for acidity (note 3).

The residue in the reaction vessel is at a temperature of 19° C. Methanol, 200 mL is charged, followed by di-t-butyldicarbonate, 62.67 grams (286.8 mmol) as a neat semi-solid. Another charge of 380 mL methanol is then added. The resulting solution is cooled to 0° C. (ice/methanol bath) When the temperature has equilibrated, triethylamine, 31.03 grams (306.6 mmol) is added dropwise over 30 minutes to maintain the reaction temperature below 1° C. Upon complete addition, the cooling bath is replaced with an ice/water bath. The reaction temperature is allowed to rise slowly to ambient temperature over 14 hrs (note 4). Gentle gas evolution is noted within 20 minutes of complete triethylamine addition.

At the end of the 14 hour aging period, the temperature of the reaction mixture is again lowered to 0° C. Solid potassium carbonate, 118.63 grams (858.3 mmol) is added portionwise over 20 minutes (no exotherm observed). Temperature is maintained at 0°–5° C. for 30 minutes followed by warm up to 20° C. over 1.5 hours. Reaction completion is monitored by TLC (note 4). After 26.5 hours at 20° C., the conversion of bromoacetate/bromohydrin mixture to epoxide is complete.

A 2000 mL 3-neck round bottom quench flask equipped with mechanical overhead stirrer and PVDF-coated type-K thermocouple probe is charged with 600 mL toluene and 600 mL water. Stirring is initiated. The reaction mixture is poured into the quench mixture over 7 minutes. An ice/water bath is used to maintain temperature between 20°–25° C. Stirring is discontinued and phase separation occurs rapidly. The layers are separated and the aqueous layer is extracted twice with 200 mL portions of toluene. The combined toluene extract is back extracted once with 200 mL water, then concentrated to dryness at a bath temperature of 60° C. and pressure of 80 mm Hg. The residue is dissolved in toluene, 200 mL and concentrated a second time. The white solid residue is dried at ambient temperature and ca. 80 mm Hg pressure overnight, providing a final weight of 64.68 grams, mp 112°–119° C. (uncorrected). This crude product is substantially pure by HPLC (85% based on peak area normalization) (note 5).

A sample of the crude product weighing 1.1 g is crystallized by heating to 60° C. in 4.5 mL toluene. Recovery of one crop of product at ambient temperature gives 600 mg. HPLC analysis establishes a purity of 98.6% (by area normalization). mp 123°–125° C. (uncorrected); $[\alpha]_D^{25}$=−7.30 (c=5.0 in methanol); combustion analysis (% cal'd , % found): C 68.42,68.57H 8.04,7.94N 5.32,5.35 ; MS (CI, methane) MH$^+$ expected:264, found:264. Proton NMR: (CDCl$_3$ solution) ppm downfield shift from TMS, #H's, multiplicity: 1.21,9H,singlet; 2.78,2H,multiplet; 2.94,3H, multiplet; 3.7,1H,br.singlet; 4.45,1H,br.singlet; 7.2–7.35, 5H,multiplet.

NOTES note 1: charge weight from cylinder is corrected for the increase in the scrubber weight. note 2: the disappearance of aminodiol is conveniently monitored by TLC (silica gel 60 with fluorescent indicator; mobile phase is dichloromethane:methanol:conc. ammonium hydroxide (80:20:0.3 v/v;chromatogram developed either with iodine or by spraying with 4% w/v solution of phosphomolybdic acid in ethanol followed by heating); R$_f$ of aminodiol is 0.5). The TLC sample is prepared by adding 1 part reaction aliquot to 3 parts conc. ammonium hydroxide.

note 3: An accurately weighed aliquot of the distillate is quantitatively transferred to an erlenmeyer flask with 30 mL methanol and diluted with 250 mL deionized water. Standardized 1N sodium hydroxide solution, 25 mL is added using a volumetric pipet. Phenolphthalein indicator is added and the resulting mixture titrated with standardized 1N hydrochloric acid. The average of two determinations indicates 17.2 milliequivalents of acid present in the distillate. The charge of triethylamine in the next step is corrected for this amount.

note 4: progress in the acylation of the amine and subsequent ring closure of the bromide mixture to the epoxide is conveniently monitored by TLC (silica gel 60 with fluorescent indicator; mobile phase is 2:1 v/v hexanes/ethylacetate; chromatogram developed by spraying with 4% w/v solution of phosphomolybdic acid in ethanol followed by heating; R$_f$ values for the intermediate N-BOC-bromohydrin, N-BOC-epoxide and intermediate N-BOC-bromoacetate are 0.42,0.51,0.63 respectively.

note 5 : HPLC conditions column: Rainin microsorb C-18 RP 80-2225-C5 with guard column detector: UV at 210 nm sample loop: 20 microliters mobile phase: 1:1 acetonitrile/water flow rate: 1 mL/min.

sample concentration: 0.5 mg/mL in mobile phase retention time of N-BOC-epoxide: ca. 12 min.

EXAMPLE 2

This example demonstrates the direct preparation of a simple amide derivative of α-phenylmethyloxiranemethanamine without urethane protection and deprotection steps.

Preparation of [S-(R*,R*)-N-(1-oxiranyl-2-phenylethyl)-2-(2,6-dimethylphenoxy)]acetamide Step 1:
Bromination of Aminodiol
Preparation of a mixture of S-(R*,R*)-β-amino-α-bromomethylbenzenepropanol hydrobromide and S-(R*,R*)-β-amino-α-bromomethylbenzenepropylacetate hydrobromide A dry 100 mL 3-neck round bottom flask containing a magnetic stir bar is charged with S-(R*,R*)-3-amino-4-phenyl-1,2-butanediol prepared in Example 1, step 2, 5.4385 grams (30.1 mmol) and is sealed with a rubber septum prior to being purged with nitrogen. The flask is cooled with an ice bath for about 15 minutes. A solution of hydrogen bromide in acetic acid (30 wt %), 34.396 grams ( 127.5 mmol, ca. 25 mL) is then added and stirring is initiated as soon as it is possible. The temperature rises to a maximum of 35° C. and then drops back to 13° C. after 5 minutes from the beginning of the addition. At this point the cooling bath is removed and the internal temperature allowed to rise to 24° C. Stirring is continued for four days at ambient temperature. The reaction vessel is fitted with a short path distillation apparatus. Heating is initiated and the pressure is lowered until steady distillation occurs at 45°–50° C. When distillation ceases at this temperature, the apparatus is vented to a nitrogen atmosphere and 20 mL of toluene is added. Distillation is then resumed under the same conditions. This operation is continued until the distillate is no longer acidic (a total of five toluene charges). The remaining residue is 19 wt % solids and is used directly in the acylation step which follows. A small sample of this residue is subjected to high vacuum to remove the solvent. This sample is characterized by proton NMR and chemical ionization MS. The results are consistant with those expected for a mixture of the aminobromohydrin and its acetate ester as hydrobromide salts.

Step 2:
Acylation of crude bromination product
The crude product residue from step 1 is diluted with dichloromethane, 26 mL and the resulting mixture is stirred under a nitrogen atmosphere while the flask is cooled in an ice bath.

2,6-dimethylphenoxyacetylchloride is prepared in a separate vessel as follows: 2,6-dimethylphenoxyacetic acid, 5.4060 grams (29.99 mmol) is charged to a 50 mL round bottom flask equipped with a teflon-coated magnetic stir bar. Toluene, 15 mL is added stirring is initiated and thionyl chloride, 9.0 mL (123.3 mmol) is added followed by one drop of N,N-dimethylformamide at ambient temperature. After seven hours, the reaction mixture is heated to 65° C. for thirty minutes and allowed to cool to ambient temperature. The solution is concentrated at 60° C. and ca. 60 mm Hg pressure to remove all volatiles. The residue is diluted with toluene, 25 mL and reconcentrated. This is repeated a second time to give a final residue.

The internal temperature of the step 1 product solution is 4.8° C. when the acid chloride residue is added via cannula transfer using nitrogen pressure. Dichloromethane, 10 mL is used to rinse the transfer line and vessel. The internal temperature is allowed to come down to 3.5° C. before dropwise addition of triethylamine, 6.05 grams (59.79 mmol) is begun. This addition requires 20 minutes and the internal temperature does not exceed 8° C. during this time. After the addition is complete, the reaction mixture is allowed to warm to ambient temperature over 15 hours. Water, 20 mL is added followed by additional dichloromethane, 30 mL. A solid fraction A is collected by filtering the mixture. This is rinsed with water and dichloromethane. It is dissolved in ethylacetate and again concentrated to dryness. The white crystalline solid weighs 1.1247 grams. This material is characterized by proton NMR, chemical ionization MS and TLC (note 1). The results indicate this material is nearly pure acylated aminobromohydrin.

The filtrate layers are separated. The aqueous layer is extracted twice with dichloromethane and the extracts combined with the organic layer from the original filtrate. The resulting solution is extracted twice with saturated aqueous sodium bicarbonate and twice with saturated aqueous sodium chloride solutions and finally dried over anhydrous magnesium sulfate. Filtration and concentration of the filtrate gives a white solid fraction B, 11.56 grams. This material is characterized by proton NMR, chemical ionization MS and TLC (note 1). The results indicate it is a mixture of the acylated aminobromohydrin acetate ester (major component) and the acylated aminobromohydrin (minor component). This mixture is used directly to prepare the epoxide in step 3.

Step 3:
Epoxide formation from crude bromides
The mixture of bromides fraction B from the previous step, 112.4 mg is suspended in methanol, 1 mL and the vessel containing the mixture cooled in an ice bath. Solid potassium carbonate, 76.2 mg (0.55 mmol) is added in one portion while stirring. After five minutes the cooling bath is removed and the reaction mixture allowed to warm to ambient temperature. When 35 minutes has elapsed since the addition of the base, an aliquot of the reaction mixture is removed and examined by TLC (note 1). Results indicate complete consumption of the bromides. At one hour after addition of base, the reaction is worked up by addition of ether, 2 mL followed by water, 6 mL. The two layers are separated and the aqueous layer extracted twice with 2 mL portions of ether. The ether extracts are combined with the original organic layer and the combined solution dried over anhydrous sodium sulfate. Filtration of the salts and concentration of the filtrate at reduced pressure gives a colorless residue weighing 81.7 mg. This material is characterized by proton NMR and chemical ionization MS. The results indicate the product is pure epoxide.

Characterization:
CIMS: expected molecular ion=325; found MH$^+$=326
Proton NMR: (CDCl$_3$ solution) ppm downfield shift from TMS,
H's, multiplicity: 2.09,6H,singlet; 2.88,2H,doublet; 2.9–3.2,3H,doublet of doublets, multiplet, doublet of doublets; 4.19,2H,ab quartet; 4.21,1H,multiplet; 6.88,1H,br. doublet; 6.98,3H,multiplet; 7.27,5H,multiplet.

Note 1: TLC conditions
solid phase: silica w/fluorescent indicator
eluent: 3:1 (v/v) hexanes in ethylacetate
developer: iodine
bromohydrin Rf=0.26
bromohydrin acetate Rf=0.50
epoxide Rf=0.28

EXAMPLE 3

This example demonstrates the direct preparation of an N-acylated aminoacid derived amide derivative of α-phenylmethyloxiranemethanamine without urethane protection and deprotection steps.

Preparation of N-(quinolin-2-ylcarbonyl)-L-valine
S-(R*,R*)-(1-oxiranyl-2-phenylethyl)amide.

Step 1:
Acylation crude bromination products

A 100 mL three neck round bottom flask equipped with teflon-coated magnetic stir bar, nitrogen inlet and PVDF-coated type-K thermocouple probe is charged with N-(2-quinolinylcarbonyl)-L-valine, 1.00 grams (3.67 mmol) and tetrahydrofuran, 7.5 mL. The reaction vessel is purged with nitrogen, stirring is initiated and the flask is cooled. When the internal temperature reaches −3° C., N-methylmorpholine, 404 mcL (3.67 mmol) is added to the solution over a five minute period. This is followed by dropwise addition of isobutylchloroformate, 477.4 mcL (3.67 mmol) over a fifteen minute period. During the addition and for an additional twenty minutes, the internal temperature is maintained between −1° and −3° C. After this time a solution of the aminobromohydrin acetate hydrobromide salt (purified from a crude bromination product by crystallization from iso-propanol), 1.348 grams (3.67 mmol) in tetrahydrofuran, 5 mL prepared in a separate vessel is added over two minutes. Additional tetrahydrofuran, 2.5 mL is used to rinse the transfer line and vessel into the reaction vessel. The temperature is still −3° C. when another charge of N-methylmorpholine, 404 mcL (3.67 mmol) is added dropwise. This addition requires 40 minutes in order to maintain temperature below −1° C. When the addition is completed, the reaction mixture is kept at this temperature another 30 minutes. Analysis of a reaction aliquot by TLC confirms the complete consumption of the amine. Ethylacetate, 30 mL is added and the resultant mixture allowed to warm to ambient temperature. It is then extracted three times with 4 mL portions of water, dried over anhydrous sodium sulfate, filtered and concentrated at 60° C. and 60 mm Hg pressure. The recovered solid is dried at ambient temperature and 0.5 mm Hg pressure. The final weight is 1.9843 grams. A sample of the crude product, 1.8843 grams is crystallized by dissolving it in hot 50% (v/v) ethylacetate in hexanes, 30 mL and allowing the solution to cool to ambient temperature. The crystalline product is collected by filtration, rinsed with 20% (v/v) ethylacetate in hexanes, 5 mL and dried at ambient temperature and 0.1 mm Hg pressure overnight. The final weight is 1.1341 grams. This product is characterized by proton and carbon NMR, IR and CIMS. The data are consistant with substantially pure acylated bromohydrin acetate. This product is used without purification in step 2.

Step 2:
  epoxide ring formation
  A 100 mL round bottom flask equipped with teflon-coated magnetic stir bar is charged with the acylated bromohydrin acetate from step 1, 1.00 grams. Methanol, 18.5 mL is added and stirring is initiated. The suspension is cooled to an internal temperature of −8° C. and held for twenty minutes. Potassium carbonate, 512 mg is added portionwise over five minutes at this temperature. One hour after the addition has been completed, an aliquot of the reaction mixture is withdrawn and examined by TLC. The acylated bromides are completely consumed. The reaction mixture is diluted with ethylacetate, 40 mL with continued stirring at −8° C. for an additional ten minutes. The mixture is then warmed to 20° C. and all volatiles removed at this temperature to a minimum pressure of 60 mm Hg. The residue is resuspended and concentrated twice more from 20 mL portions of ethylacetate. The new residue is suspended by stirring in ethylaceate, 40 mL for ten minutes and then filtered. The collected solid is rinsed with 10 mL ethylacetate and the combined filtrate concentrated at 20° C. and a minimum pressure of 60 mm Hg to remove all volatiles. The residue is finally concentrated twice from 10 mL portions of hexanes and dried at ambient temperature and 0.1 mm Hg pressure for four hours. The weight of the product is 767.3 mg. It is substantially pure epoxide by TLC (note 1) and proton NMR characterization. A sample of this product, 744.8 mg is crystallized from a hot solution in ethylacetate, 4 mL and hexanes, 12 mL. The purified product after drying is 550 mg.

Characterization:
Proton NMR: (CDCl$_3$ solution) ppm downfield shift from TMS,
H's, multiplicity: 0.90,3H,doublet; 0.97,3H,doublet; 2.37,1H,multiplet; 2.78–3.05,5H,overlapping multiplets; 4.08,1H,multiplet; 4.37,1H,doublet of doublets; 6.24,1H,br.doublet;6.97,1H,multiplet; 7.06,2H,overlapping doublet of doublets; 7.15,2H,doublet; 7.66,1H,multiplet; 7.82,1H,multiplet; 7.92,1H,doublet; 8.17,1H,doublet; 8.26,1H,doublet; 8.36,1H,doublet; 8.56,1H,br.doublet.

Note 1: TLC conditions
  solid phase: silica w/fluorescent indicator
  eluent: 10% (v/v) methanol in chloroform
  developer: phosphomolybdic acid
  epoxide Rf=0.68
  acylated bromohydrin acetate Rf=0.83

EXAMPLE 4

This example demonstrates the alternative sequence using three discrete steps to prepare a urethane-protected α-(phenylmethyl)oxiranemethanamine from aminodiol compound of formula 4.

Preparation of [S-(R*,R*)]-(1-oxiranyl-2-phenylethyl)carbamic acid 1,1-dimethylethyl ester Step 1:
  Preparation of [S-(R*,R*)-(4-phenyl-1,2-dihydroxybutane-3-yl) carbamic acid 1,1-dimethylethyl ester
  A 500 mL three-neck round bottom flask is equipped with mechanical overhead stirrer and two rubber septa, one fitted with a type-K thermocouple probe and a syringe needle vented to a nitrogen supply via an oil bubbler. The flask is charged with S-(R*,R*)-3-amino-4-phenyl-1,2-butanediol, 20.0 grams (110.35 mmols) and purged with nitrogen. Toluene, 100 mL is charged and the resulting mixture stirred. A separate 250 mL round bottom flask is charged with di-tert-butyldicarbonate, 25.06 grams, (111.37 mmols) and toluene, 50 mL. The resulting solution is added dropwise over ten minutes to the suspension of aminodiol in toluene. This is followed by transfer of two 25 mL toluene rinses of the addition flask and transfer line. This is accomplished via cannula using nitrogen pressure. The internal temperature of the aminodiol suspension during the addition is 21° C. During the next one hour and twenty minutes the temperature gradually rises to 31° C. and gas evolves steadily. The mixture becomes thick and unstirrable. Additional toluene, 50 mL is added, stirring is terminated and the mixture is allowed to stand for fourteen hours at ambient conditions. Stirring is resumed and the mixture is heated to 71° C. to produce a clear solution. This is transferred to a 1000 mL round bottom flask and the hot solution is concentrated at 70° C. and a pressure of 180 mm Hg until distillation ceases. This produces a white solid which dried under vacuum for an additional two hours. The final weight is 31.37 grams (101% of theory).

Step 2:
  Preparation of [S-(R*,R*)-(4-phenyl-1-(4-methylbenzenesulfonyloxy)-2-hydroxybutane-3-yl) carbamic acid 1,1-dimethylethyl ester
  A 250 mL three-neck round bottom flask is equipped with mechanical overhead stirrer and two rubber septa, one fitted with a type-K thermocouple probe and a syringe needle vented to a nitrogen supply via an oil bubbler. The flask is charged with the product from step 1, 19.99 grams (71.05 mmols) and purged with nitrogen. Pyridine, 40 mL is charged to the reaction vessel, stirring is initiated and the vessel is placed in a thermostatted cooling bath at −8.5° C. The resulting thick slurry is diluted with an additional 5 mL pyridine to facilitate stirring. A separate 50 mL round bottom flask is charged with para-toluenesulfonylchloride, 13.96 grams, (73.24 mmols) and pyridine, 15 mL. The resulting solution is added dropwise over forty-five minutes to the suspension of the diol in pyridine. This is followed by transfer of two 5 mL pyridine rinses of the addition flask and transfer line. This is accomplished via cannula using nitrogen pressure. The internal temperature of the reaction mixture during the addition is prevented from exceeding −5° C. After the last transfer is complete, the reaction is maintained between −8° and −10° C. for twenty-four hours. TLC analysis at this point confirms that no diol remains in the reaction mixture. Water, 40 mL is added dropwise over thirty minutes, maintaining the internal temperature between −5° and −10° C. Stirring is continued at this temperature for another fifteen minutes, then toluene, 100 mL is added. The cold mixture is poured into a 500 mL separatory funnel containing 100 mL toluene. The reaction flask is rinsed with another 20 mL toluene into the funnel. The layers are separated and the aqueous layer is extracted twice with 100 mL portions of toluene. The combined toluene layers are kept cold (0° C.) and extracted twice with 400 mL portions of cold (5° C. ) 1.0M aqueous phosphoric acid, once with 200 mL water and once with 200 mL saturated sodium chloride solution. During the extractions, a solid begins to crystallize from the toluene solution. The mixture is diluted with additional toluene, 1000 mL and dichloromethane, 50 mL. The result is dried over anhydrous sodium sulfate and filtered. The collected solid is rinsed well with dichloromethane. The combined filtrate is concentrated at reduced pressure (water bath at 50° C.) to give a residual white solid weighing 30.08 grams (97% of theory). The product is characterized by proton NMR and TLC which indicates that it is substantially pure and consistant with a previously prepared reference sample.

Step 3:

epoxide ring formation

To a 250 mL round bottom flask equipped with teflon-coated magnetic stir bar and nitrogen inlet is charged 10.0 grams (23 mmols) of the product toluenesulfonate ester from step 2, solid potassium carbonate, 3.2 grams (23 mmols) and methanol, 100 mL. The resulting mixture is stirred at ambient temperature. After two hours, TLC analysis of a reaction aliquot reveals the absence of toluenesulfonate ester. The reaction mixture is vacuum filtered and the collected solid rinsed with methanol. The combined filtrates are concentrated at 40° C. and 100 mm Hg pressure. The solid residue digested with boiling ethylacetate for ten minutes and filtered hot. The collected solid is digested as above and again filtered hot. The combined filtrates are concentrated at 40° C. and 100 mm Hg pressure and the solid residue dried at ambient temperature and a pressure of 100 mm Hg for eighteen hours. The final product is a white solid weighing 5.28 grams (87% of theory). The product is characterized by proton NMR and TLC which indicates that it is substantially pure and consistant with a previously prepared reference sample.

EXAMPLE 5

This example illustrates the utility of a compound of formula A, [S-(R*,R*)]-(1-oxiranyl-2-phenylethyl)carbamic acid 1,1-dimethylethyl ester to produce an HIV protease inhibitor.

Preparation of N-{1(S)-[[[3-[2(S)-{[(1,1-dimethylethyl)amino]carbonyl}-4(R)-[4-(pyridinylmethyl)oxy]-1-piperidinyl-2(R)-hydroxy-1 (S)-(phenylmethyl)propyl]amino]carbonyl]-2-methylpropyl}-2-quinolinecarboxamide.

Step 1:

Coupling of the epoxide with an amine fragment.

A solution of water in isopropanol (10% v/v) (1.5 L) is heated at reflux for 2.5 hours under argon atmosphere then cooled to room temperature. [S-(R*,R*)]-(1-oxiranyl-2-phenylethyl)carbamic acid 1,1-dimethylethyl ester (271.1 g) and 2(S)-{[(1,1-dimethylethyl)amino]carbonyl}-4(R)-[4-(pyridinylmethyl)oxy]piperidine (300.1 g) are added under the exclusion of air and the mixture stirred for 96 hours under positive argon pressure. The solvents are removed under reduced pressure at 32° C. The residue is redissolved in ethyl acetate (1.84 L) and cooled in an ice water bath. The organic solution is extracted with 1N $KH_2PO_4$ (3×1.012 L) followed by the addition of 2.5N HCl (1150 mL) and 10% HCl (598 mL) keeping the internal temperature below 20° C. The organic phase is removed and the aqueous phase is extracted with ethyl acetate (3×460 mL). Concentrated HCl (368 mL) is added giving a final temperature of 21.1° C. and pH of 0. The resulting mixture is allowed to warm to room temperature and stir overnight under positive nitrogen pressure. The reaction mixture is cooled in an dry ice-acetone bath and solid sodium hydroxide pellets (258 g) added followed by 40% sodium hydroxide (570 mL) keeping the internal temperature below 21° C. The final pH is 11–12. The product is extracted into ethyl acetate (1×1 L, 1×1.5 L), and the combined organic solution extracted with saturated brine (1 L). The resulting organic solution is dried over anhydrous magnesium sulfate (138.09 g) and filtered through silica gel (350 g). The filter cake is further washed with ethyl acetate (3.5 L) and concentrated to dryness under reduced pressure at 40° C. The solids are further vacuum dried giving 150.27 g of product.

The filter cake is resuspended in ethyl acetate (3 L) and stirred for one hour. The mixture is then filtered. The filter cake is washed with ethyl acetate (300 mL) and again resuspended in 20% methanol in ethyl acetate (3 L) with stirring. The mixture is then filtered. The filter cake is washed with ethyl acetate (300 mL). The filtrate is concentrated to dryness under reduced pressure at 40° C. and further vacuum dried to give an additional 78.15 g of product.

The acidic ethyl acetate extracts are concentrated under reduced pressure and the residue charged to the reaction flask. The flask is cooled in an ice water bath. Concentrated HCl (184 mL) is charged keeping the internal temperature below 20° C. Allow the mixture to warm to room temperature and stir overnight under positive nitrogen pressure. Cool the reaction mixture in a dry ice-acetone bath, and add sodium hydroxide pellets (129 g) followed by 40% sodium hydroxide (253 mL) until the pH reaches 12–13. During this time the internal temperature is kept below 20° C. The product is extracted into ethyl acetate (1×750 mL, 1×500 mL). The combined organic solution is extracted with saturated brine (500 mL) then dried over anhydrous magnesium sulfate (70.66 g). This mixture is filtered through silica gel (177.07 g). The filter cake is washed with 20% methanol in ethyl acetate (2 L). The combined filtrates are concentrated to dryness at 40° C. under reduced pressure followed by further vacuum drying. This gives a recovered weight of 134.63 grams. The material is dissolved in a 2/1 mixture of ethyl acetate and methanol (300 mL) and filtered through a column of silica gel (500 g) eluting with 70% isopropanol in ethyl acetate. The effluent fractions are combined and concentrated under reduced pressure at 40° C. Further vacuum drying yields an additional 87.40 g of product. The total weight of recovered product is 315.82 grams.

An additional larger reaction produces another 600.27 grams of product. The two batches are combined for the next step.

Step 2:

Further purification of the above coupling product.

The above combined product, 916.09 g is transferred to a 7-L rotary evaporation flask using THF (2548 g). The resulting suspension is concentrated by distillation using the rotary evaporator. The nearly dry residue is redissolved in a mixture of deionized water (400 mL) and dichloromethane (5.6 L). This new mixture is concentrated in the same manner until all the dichloromethane and THF have been distilled out.

The residue after concentration is transferred to the reaction vessel using dichloromethane (4.4 L) and deionized water (1.5 L). Stirring is initiated. The temperature of the reactor contents is 20° C.

The pH of the aqueous phase is adjusted to approximately 12–12.5 by adding 5N sodium hydroxide solution (175 mL). This addition is carried out over one hour. During this time the reactor contents are maintained in the temperature range 18°–21° C. using an ice/water bath.

The aqueous layer is removed and the organic layer is extracted with deionized water (2×1 L). The combined aqueous fractions are extracted with dichloromethane (2×1 L).

The combined dichloromethane fractions are stirred with magnesium sulfate (501.83 g). The solid is collected by filtration and rinsed with dichloromethane (1 L). The combined filtrate (transfer rinse with dichloromethane, 600 mL) is concentrated using the rotary evaporator. The residue is dissolved in THF (2 L) and concentrated as above until approximately one liter of distillate is collected. The final weight of purified product isolated is 787.54 grams.

Step 3:

Mixed anhydride mediated coupling of amine from step 2 and N-(2-quinolinecarbonyl)-S-valine.

The reaction vessel is purged and maintained under a small positive pressure of nitrogen. It is then charged with N-(2-quinolinecarbonyl)-S-valine, 211.25 g and THF, 1.3 L.

The solution resulting from the previous step is cooled by means of a dry ice/acetone bath. Charging of 4-methylmorpholine (142.76 g) commences when the internal reactor temperature is −4° C.

Charging of iso-butylchloroformate (105.76 g) from a 125 mL dropping funnel commences when the reaction temperature reaches −41° C. The addition is complete in seven minutes. Temperature is maintained during this period.

A solution is prepared by dissolving the amine from step 2 (320.15 g) in THF (650 mL). The charge of this solution to the reactor begins thirty-three minutes from the end of the previous addition. The container and transfer line are rinsed with additional THF (50 mL). This operation is completed in thirty-five minutes. The temperature during this time is maintained between −40° C. and −44° C.

The stirring reaction mixture is kept in the above temperature range for an additional thirty minutes. The cooling bath is then removed and the reaction temperature allowed to rise. It has reached 21° C. in five hours thirty minutes. Reaction progress is monitored by TLC analysis of reaction samples (see note 1).

The reaction mixture is quenched by the addition of water (500 mL) six hours, seven minutes from the beginning of the warm-up period.

The reaction mixture is concentrated by distillation at reduced pressure using the rotary evaporator (bath temp. 40° C., pressure 60 mm Hg). THF removal is complete in one hour.

The residual reaction mass is transferred back to the reaction vessel using ethylacetate (2 L). The solution is extracted with deionized water (2×1 L).

The organic solution is now extracted three times with 3N sodium hydroxide solution (2×650 mL; 1×700 mL). This operation is completed in fifty-five minutes. During this time an ice/water cooling bath is used to control internal temperature between 20° and 33° C.

The organic solution is now extracted deionized water (2×1 L). This is complete in one hour twenty minutes.

The crude product is now extracted into water by slowly adding 9.5% hydrochloric acid solution to the organic phase (1 L). This addition is exothermic and requires cooling to maintain the temperature between 15° and 18° C. The aqueous extract is separated and the organic phase extracted again with 9.5% hydrochloric acid (400 mL). The organic phase is now separated and the hydrochloric acid extracts combined in the reactor. This operation is complete in one hour, five minutes.

The combined solution of the product in hydrochloric acid is extracted with ethylacetate (3×300 mL). The aqueous solution is cooled to 2.6° C. The pH is then adjusted between 7–8 by adding 10N sodium hydroxide (425 mL). Ethylacetate (900 mL) is added to dissolve an oily solid which separates. The pH of the aqueous phase is further adjusted to 11 using 10N sodium hydroxide solution (150 mL).

The organic phase is separated and the remaining aqueous phase is extracted twice with ethylacetate (400 mL;200 mL). All ethylacetate fractions are combined and these are extracted three times with saturated sodium chloride solution (1×2 L;2×600 mL).

The organic phase is now stirred with approximately equal parts (w/w/w) silica gel (49.63 g),carbon (50.28 g) and anhydrous magnesium sulfate (50.94 g). The suspension is filtered and the collected solid rinsed with ethylacetate (200 mL).

The combined filtrate is concentrated by distillation using the rotary evaporator (bath temperature 45° C., pressure 60 mm Hg). The residue is dissolved in methanol (2 L) and concentrated as above. This yields 459.7 grams of crude product.

note 1: TLC conditions for monitoring reaction progress are as follows. Solid phase:silica gel 60 with fluorescent indicator; mobile phase: 9:1 (v/v) dichloromethane-methanol containing a trace of ammonium hydroxide; approximate $R_f$ assignments: amine,0.36; product (as dihydrochloride salt),0.40.

Step 4:

Preparation of final product dihydrochloride salt

The reaction vessel is purged and maintained under a small positive pressure of nitrogen. Crude product from step 3 (459.7 g) is transferred to the reaction vessel as a solution in methanol (510 mL). The contained weight on a dry basis is 436.4 g (the remainder of the charge weight is methanol).

Stirring is initiated and 4N HCl in dioxane solution (603 mL) is added over a one hour period. During this time, the reactor contents are maintained between 15° C. and 19° C. by means of an ice/water bath.

Immediately after the HCl addition, the reactor is charged with iso-propanol (304 mL) and additional methanol (145 mL). The mixture is heated to reflux (72° C.) over one hour and maintained refluxing for an additional forty-five minutes. Heating and stirring are then discontinued allowing the solution to cool slowly.

After twelve hours, the internal temperature is 27° C. Stirring is resumed to break up the solid mass and accelerate cooling. This continues for four hours, thirty minutes. The temperature is 23° C. The batch is filtered and the filter cake rinsed with 50% (v/v) iso-propanol/acetone (2×400 mL) and acetone (2×300 mL).

The wet solid is transferred to a glass dish and dried at 23° C. at a vacuum of 30" Hg for 23 hours. The final weight is 279.01 grams.

The above procedure is carried out on a larger scale giving an additional 724.3 grams of crude product dihydrochloride salt. The material from the two runs is combined for final purification by recrystallization as follows:

The reaction vessel is purged and maintained under a small positive pressure of nitrogen. Crude dihydrochloride salt (1.003 Kg) is transferred to the reaction vessel along with 1:2 (v/v) iso-propanol/acetone (6 L).

Stirring is initiated and the mixture is heated to 60° C. over one hour, forty minutes. This temperature is maintained during slow addition of 50% (v/v) iso-propanol/water (528 mL). The addition is complete in one hour, thirty minutes (the quantity is just enough to dissolve all solids at this temperature).

Fifteen minutes from the end of the addition, heating is discontinued and the solution allowed to cool slowly with continued stirring.

After sixteen hours the internal temperature is 22° C. An ice/water bath is used to cool the vessel. One hour later, the temperature is 10° C. The batch is filtered and the filter cake rinsed with 1:2 (v/v) iso-propanol/acetone (2×1.5 L) and with acetone (2×1 L).

The wet solid is charged to the rotary evaporator flask and suspended in iso-propanol (3 L). The suspension is concentrated to near dryness and subjected to high vacuum for thirty minutes. The final weight is 973.25 grams. A dried sample of this material establishes the dry weight (100% solids basis) to be 853.65 grams.

The reaction vessel is purged and maintained under a small positive pressure of nitrogen. The recrystallized salt (973.25 g) is transferred to the reaction vessel along with 1:2 (v/v) iso-propanol/acetone (5.1 L).

Stirring is initiated and the mixture is heated to 60° C. over one hour, forty minutes. This temperature is maintained during slow addition of 50% (v/v) iso-propanol/water (353 mL). The addition is complete in one hour, thirty minutes (the quantity is just enough to dissolve all solids at this temperature).

Fifteen minutes from the end of the addition, heating is discontinued and the solution allowed to cool slowly with continued stirring.

After sixteen hours the internal temperature is 22° C. An ice/water bath is used to cool the vessel. One hour later, the temperature is 10° C. The batch is filtered and the filter cake rinsed with 1:2 (v/v) iso-propanol/acetone (2×1.2 L) and with acetone (2×900 mL).

The wet solid is transferred to a glass dish and dried at 23° C. at a vacuum of 29–30" Hg for 24 hours. After a weight check, drying is resumed at a vacuum of 29.5" Hg for twenty-four hours at 35° C. and an additional seventeen hours cooling to 23° C. The final weight is 807.1 grams.

The purity of this product determined by HPLC is 99.6%. The salt is converted to the free base. The base is characterized by satisfactory combustion analysis, mass spectrum (chemical ionization) and NMR (600 MHz proton and 150 MHz carbon). The NMR data is correlated with a reference sample of confirmed structure established by X-ray crystallographic analysis of the dihydrochloride salt.

EXAMPLE 6

Preparation of S-(R*,R*)-3-amino-4-phenyl-1,2-butanediol ("aminodiol")

Step 1:

Aminolysis of 2R-trans-3-phenylmethyl-2-oxiranemethanol ("epoxyalcohol") with aminodiphenylmethane Into a dry 5 liter three-neck round bottom flask fitted with overhead mechanical stirrer and type K thermocouple, 897 mL of dry toluene is charged. After purging with nitrogen, the solvent is heated to 50° C. and 200 rpm stirring initiated. To the stirring toluene at 50° C., 525.60 grams (1.849 moles) of freshly distilled titanium (IV) isopropoxide is added in one portion followed by the addition of 272.08 grams (1.485 moles) of aminodiphenylmethane over 20 minutes. The stirring solution is heated to 68° C. and equilibrated at this temperature for 30 minutes. To the stirring solution of titanium (IV) isopropoxide/$Ph_2CHNH_2$ in toluene at 68° C., a solution of the epoxyalcohol, 230 grams (1.401) moles in 1077 mL of dry toluene is added over 30 minutes, keeping the temperature (internal) of the reaction at 68° C. (mild exotherm, air cooling). Twenty-five minutes after the addition is complete evolution of heat subsided and the reaction is gently heated to maintain the 68° C. temperature for an additional 20 minutes. The reaction is sampled for a completion check by TLC (note 1).

When completed (no epoxyalcohol remaining) the reaction mixture is cooled to 17° C., using an ice/water bath and 888.5 mL of 10% NaOH in saturated NaCl solution added over 25 minutes, keeping the temperature (internal) below 24° C.

The reaction mixture becomes viscous and is allowed to stir overnight. The now mobile reaction mixture is allowed to stand. The separated organic phase (top) is transferred out. The aqueous phase is extracted with 1,000 mL of toluene and the extract transferred out. The aqueous phase is stirred with an additional 1,000 mL of toluene and to this 100 grams of Celite 545 added. After stirring for 20 minutes, the emulsion is filtered. The clear filtrate is separated and the top organic phase combined with the previous extracts. The organic extracts were dried over anhydrous sodium sulfate and filtered. The filtrate is concentrated to dryness at 60° C., 50 mm Hg pressure, yielding an orange oil weighing 490.15 grams. This material is a mixture of two isomers, the desired "C-3 diphenylmethylaminodiol" and the "C-2 diphenylmethylaminodiol". The mixture is used without further purification.

The oil is assayed by proton NMR using trichloroethylene as internal standard. Yield and isomer ratio are determined by integration of benzhydryl methine resonances near 5.0 ppm vs the trichloroethylene resonance at 6.5 ppm. The assignment for the methine resonances is based on the purification and characterization of each isomer for reference purposes.

Yield of C-3 DPM-aminodiol: 60.14%

Yield of C-2 DPM-aminodiol: 14.82% C-3/C-2 ratio= 4.1:1

Characterization of product mixture:
proton NMR ($CDCl_3$ solution):
chemical shift assignment (in ppm downfield from TMS)
4.9 ppm C-3 isomer methine
5.0 ppm C-2 isomer methine
5.2 ppm diphenylmethylamine methine
CIMS (methane): expected molecular ion=347; found $MH^+$=348

Step 2:

Hydrogenolysis of diphenylmethylaminodiol mixture

A 2,000 mL stainless steel Parr reactor (model 4522) is charged with 95.68 grams of 10% palladium-on-carbon (50% water wet). The vessel is purged with nitrogen while 488.89 grams of the crude mixture of diphenylmethylaminodiols prepared in step 1 is charged as a solution in 500 mL of methanol. An additional 200 mL of methanol is charged and the vessel assembled and purged again with nitrogen. After pressure checking to 80 psi for 1 hour, hydrogen is introduced and the contents hydrogenated at 60 psi not allowing the internal temperature to rise above 35° C. The hydrogenation conditions were maintained overnight (16 hours).

A reaction sample is taken for a completion check by TLC (note 1). When complete (no detectable diphenylmethylaminodiols) the reactor is vented, purged with nitrogen and the contents filtered. The catalyst cake is washed with 600 mL of methanol and the combined almost colorless filtrate concentrated at 55° C. and 50 mm Hg pressure. This yields a suspension of white solid in oil weighing 456.35 grams. This suspension is concentrated twice from 500 mL dry toluene to give 479.17 grams of white solid in oil. This mass is allowed to cool to ambient temperature and 200 mL additional toluene is added. The suspension is stirred, filtered and air dried. The white crystalline solid product is washed twice with 200 mL toluene and air dried again. The product is finally washed two times with 200 mL portions of hexanes and dried at ambient temperature and 50 mm Hg pressure overnight. The final weight is 124.87 grams.

Theoretical yield of C3 isomer=153.36 grams Actual dry weight of C3 isomer=124.87 grams Yield=81.4%
A sample of this product is converted to the t-butylcarbamate derivative for chiral HPLC analysis.
Characterization:
 proton NMR: (DMSO $d_6$/$D_2O$ solution)
  ppm downfield shift from TMS, #H's, multiplicity: 2.40, 1H, multiplet; 2.89, 2H, multiplet; 3.31, 1H, multiplet; 3.50, 2H, multiplet; 7.26, 5H, multiplet
 carbon NMR: (DMSO $d_6$) DMSO resonance at 39.499 ppm:
  39.396, 55.585, 63.921, 74.348, 125.761, 128.153, 129.393, 140.250
 CIMS (methane): expected molecular ion=181; found $MH^+$=182
 IR (KBr pellet) $cm^{-1}$:
  3344, 3305, 3283, 3086, 2918, 2712, 1608, 1492, 1376, 1097, 1079, 1058, 751, 700
 Melting range: 109°–111° C. (uncorrected)
 Combustion analysis (% cal'd, % found): C 66.27,66.69 H 8.34,8.45N 7.73,7.83
 Specific rotation $([°]_D^{25})$: −34.68° (c=2.01, methanol)
 Chiral HPLC: analysis of t-butylcarbamate derivative
  column: Chiralcel OD, 25 cm×4.6 mm mobile phase: hexane-ethanol (98:2) flow rate: 1.0 mL/min. temperature: 40° C. detector: UV @ 254 nm 0.1 aufs

|  | $t_r$ | k' | R | T |
|---|---|---|---|---|
| racemate | 28.77 | 6.36 | 1.084 | 2.16 |
|  | 32.05 | 7.20 | 1.79 |  |
| product | 28.78 |  |  |  | no peak detected @ 32.05 min.
$t_r$ = retention time in minutes; k' = capacity factor; R = resolution; T = tailing factor.

Note 1: TLC conditions
 solid phase: silica w/fluorescent indicator
 eluent: 25% (v/v) acetone in hexanes
 developer: iodine or phosphomolybdic acid
 C-3 DPM-aminodiol Rf=0.24
 C-2 DPM-aminodiol Rf=0.34
 epoxyalcohol Rf=0.34
 aminodiphenylmethane Rf=0.47
 aminodiol (product) Rf=immobile
(the two components at Rf 0.34 are distinguished by intensity of development with iodine and phosphomolybdic acid)

EXAMPLE 7

This example demonstrates the utility of benzylamine in the overall conversion of the compound of formula 5 to the compound of formula 4.

Preparation of S-(R*,R*)-3-amino-4-phenyl-1,2-butanediol ("aminodiol")

Into a dry 25 mL three-neck round bottom flask equipped with teflon-coated magnetic stirrer and type K thermocouple, 5 mL of dry toluene is charged. After purging with nitrogen, stirring is initiated and the solvent is heated to and maintained at 55° C. using an electric mantle and PID controller.

To the stirring toluene at 55° C., 0.718 grams (6.7 mmols) of benzylamine is added by syringe followed by distilled titanium (IV) isopropoxide, 2.21 grams (7.78 mmols). After 15 minutes, a dry solution of the epoxyalcohol, 1.003 grams (6.11 mmols) in 3 mL of toluene is added over 2 minutes from a separate flask via cannula using nitrogen pressure. The temperature (internal) of the reaction is maintained between 55°–60° C. during the addition. A total of 1 mL dry toluene is used in two equal portions to rinse the addition flask and transfer line into the reaction vessel. After 8 hours at 55° C. the mixture is cooled over twenty minutes to 26° C. and quenched by adding 3.8 mL 10% sodium hydroxide solution saturated with sodium chloride. The result is stirred overnight.

The separated organic phase (top) is transferred out of the reaction vessel and the semi-solid residue is extracted three times with 10 mL portions of toluene. The combined extracts are stirred with one gram of Celite 545 and the slurry is filtered over a bed of additional Celite 545 (0.5 grams). The clear filtrate is concentrated at reduced pressure giving a residue weighing 1.58 grams.

This product is used without further purification in the hydrogenation step.

The above crude product, 1.34 grams is quantitatively transferred to a 50 mL Hastalloy autoclave using 7 mL methanol. The catalyst, 20% palladium on carbon (50% wet with water), 121.87 mg is charged to the autoclave which is then sealed. The vessel is purged first with nitrogen then hydrogen. The pressure is adjusted to 60 psi and stirring is initiated (1474 rpm). The hydrogenation is allowed to proceed for 64 hours at ambient temperature. Stirring is terminated and after an additional 5.5 hours with the vessel isolated from the hydrogen supply no pressure drop is observed. The vessel is vented, purged with nitrogen and the contents removed and filtered over a bed of Celite 545. The filtrate is concentrated at reduced pressure and the residue redissolved and concentrated from toluene twice. This results in a white solid which is reslurried in toluene, collected by filtration, rinsed with toluene then hexane and dried. The final solid weighs 395.6 mg representing an overall yield of 42% from the epoxyalcohol. Melting point and proton NMR characterization confirm the solid is the intended product.

I claim:

1. A process for forming an epoxy compound of the formula (A):

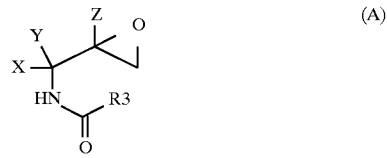

wherein X is: hydrogen, a straight or branched chain alkyl group containing from 1 to 8 carbon atoms, cycloalkyl containing from 3 to 8 carbon atoms, cycloalkylalkyl, arylalkyl, aryl wherein aryl is phenyl, naphthyl or a 5–6 membered heterocyclic ring containing one or two heteroatoms selected from N, O and S and said aryl group is optionally substituted with one or more alkyl groups, halogens, amino or hydroxy groups, arylheteroatomalkyl group where the heteroatom is nitrogen, oxygen or sulfur;

Y and Z are both hydrogen and can independently have a stereochemical orientation which results in either the (R) or (S) configuration at the carbon atoms to which they are bound; and $R_3$ is a lower alkoxy group containing 1 to 8 carbon atoms which can form a straight or branched chain, part of a ring or a combination thereof; an alkenylmethoxy group; an arylalkoxy group wherein the aryl portion is optionally substituted with halogen atoms, lower alkoxy or lower alkyl groups of from one to five carbon atoms or combinations thereof and the alkyl portion of the arylalkoxy group contains from 1 to 5 carbon atoms; an aryloxyalkyl group wherein the aryl portion is optionally substituted with halogen atoms, lower alkoxy or lower alkyl groups of from one to five carbon atoms or combinations thereof and the alkyl portion contains from 1 to 5 carbon atoms; aryl optionally substituted with heteroatoms where the heteroatom is nitrogen, oxygen or sulfur, alkyl groups, haloalkyl groups and halogen, amino, or hyrdoxy groups; acylated alpha-aminoalkyl wherein the alkyl group is defined by those found in the naturally occurring aminoacids and the acyl group is derived from a carboxylic acid or carbonic acid ester; the process comprising:

activating the terminal hydroxy group of an aminodiol of the formula:

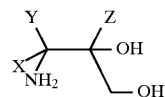

Formula 1 wherein X, Y and Z are as defined above;
N-acylating the activated aminodiol to form the activated precursors of Formula A; and
reacting said activated precursors to Formula A with a base to form a compound of Formula A.

2. A process as defined in claim 1 wherein X is arylalkyl wherein the aryl group is phenyl or naphthyl which may be substituted with one or more alkyl groups, halogens, haloalkyl groups, amino or hydroxy groups; cycloalkylalkyl groups of 3 to 8 carbon atoms and arylheteroatomalkyl group wherein the heteroatom is one or more of N, S, or O.

3. A process as defined in claim 1 wherein X is

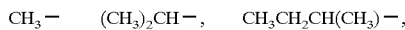

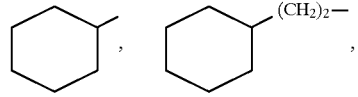

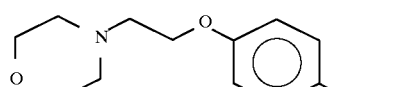

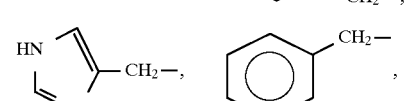

-continued

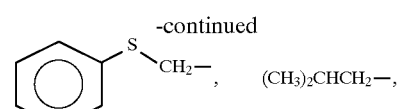

4. A process as defined in claim 1 wherein the $R_3C(O)$ is:

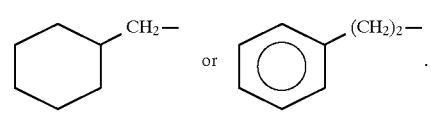

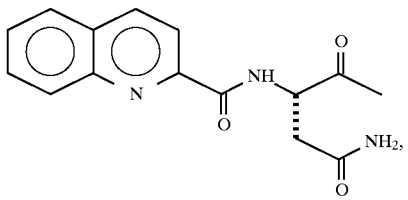

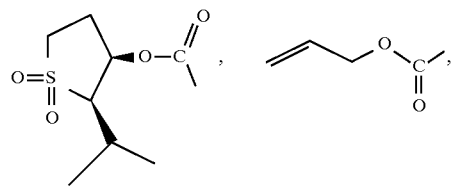

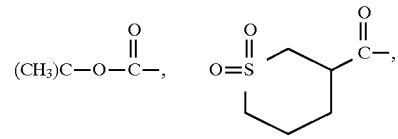

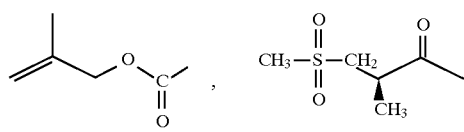

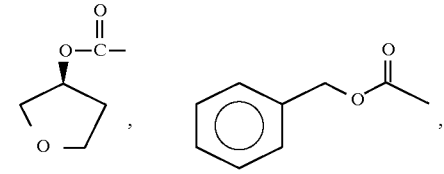

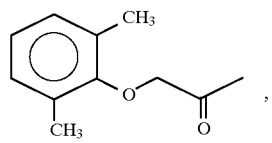

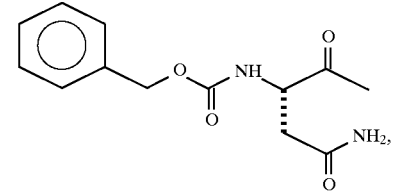

-continued

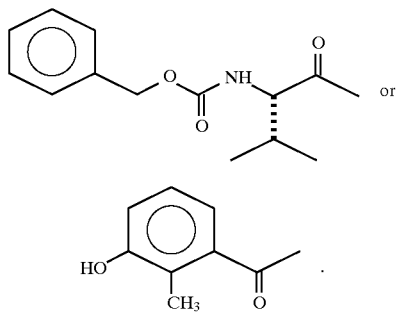

5. A process as defined in claim 1 wherein the epoxy compound is selected from the group consisting of:
   [S-(R*,R*)]-(1-oxiranyl-2-phenylethyl) carbamic acid 1,1-dimethylethyl ester,
   [S-(R*,R*)]-(1-oxiranyl-2-phenylethyl) carbamic acid phenylmethyl ester,
   [R-(R*,S*)]-(1-oxiranyl-2-phenylethyl) carbamic acid 1,1-dimethylethyl ester, and
   [R-(R*,S*)]-(1-oxiranyl-2-phenylethyl) carbamic acid phenylmethyl ester.

6. A process as defined in claim 1 wherein the epoxy compound is selected from the group consisting of:
   [S-(R*,S*)]-(1-oxiranyl-2-phenylthioethyl) carbamic acid 1,1-dimethylethyl ester,
   [S-(R*,S*)]-(1-oxiranyl-2-phenylthioethyl) carbamic acid phenylmethyl ester,
   [3S-[3R*(1R*,2R*)]]-(1-oxiranyl-2-phenylethyl) carbamic acid tetrahydro-3-furanyl ester, and
   [2R-[2R*,3R*(1S*,2S*)]]-(1-oxiranyl-2-phenylethyl) carbamic acid tetrahydro-[2-[(1-methyl)ethyl]-3-thienyl ester, S,S-dioxide.

7. A process as defined in claim 1 wherein the epoxy compound is selected from the group consisting of:
   N-(quinolin-2-ylcarbonyl)-L-valine S-(R*,R*)-(1-oxiranyl-2-phenylethyl)amide, and
   $N^2$-(quinolin-2-ylcarbonyl)-L-asparagine S-(R*,R*)-(1-oxiranyl-2-phenylethyl)amide, N-[S-(R*,S*)-(1-oxiranyl-2-phenylthioethyl)]-3-hydroxy-2-methylbenzamide.

8. A process as defined in claim 1 wherein the activation step comprises reacting the aminodiol with hydrobromic acid and a carboxylic acid selected from the group consisting of formic acid, acetic acid and propionic acid.

9. A process as defined in claim 5 wherein the carboxylic acid is acetic acid.

10. A process as defined in claim 1 wherein the acylation step comprises mixing the activated aminodiol with a solvent and an acylating agent.

11. A process as defined in claim 10 wherein the acylating agent is an acyl halide, a dicarbonic acid ester, or an intermediate generated from N-protected aminoacids.

12. A process as defined in claim 10 wherein the solvent is methanol, toluene, dichloromethane, tetrahydrofuran, dimethylformamide, acetonitrile or water.

13. A process as defined in claim 1 wherein the epoxide is formed in situ by reacting its activated precursor with a mixture of a base and a fragment for forming an aspartyl protease inhibitor or an advanced intermediate thereto.

14. A process as defined in claim 1 wherein the aminodiol is a compound of the formula

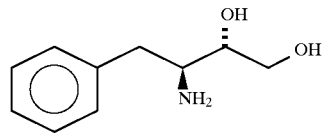

or its enantiomeric form.

15. A process as defined in claim 13 wherein the aminodiol is prepared by reacting a glycidol compound of the formula:

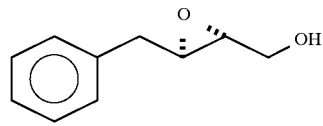

or its enantiomeric form respectively with an amine of the formula: $R_1R_2NH$ wherein $R_1$ and $R_2$ are independently selected from the group consisting of hydrogen, arylalkyl or di-(aryl)alkyl in the presence of a catalyst to obtain a mixture of compounds of the following structures:

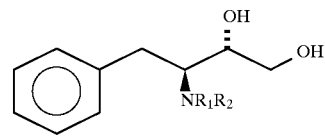

6

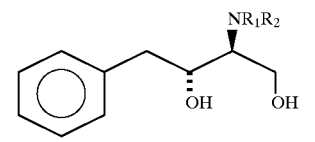

7 wherein $R_1$ and $R_2$ are as hereabove defined;
hydrogenating the mixture of formula I and II; and
crystallizing the hydrogenated mixture to obtain the aminodiol substantially free of its enantiomer and the hydrogenated derivative of Formula II.

16. A process as defined in claim 15 wherein $R_1$ is hydrogen and $R_2$ is diphenylmethyl.

17. A process as defined in claim 15 wherein $R_1$ is hydrogen and $R_2$ is benzyl.

18. A process as defined in claim 15 wherein the catalyst is a titanium (IV) catalyst.

* * * * *